May 1, 1956 G. MERRILL Plant Pat. 1,472

PEACH TREE

Filed March 17, 1955

WITNESS

Addison E. Avery

INVENTOR

Grant Merrill

Webster & Webster

ATTYS.

United States Patent Office

Plant Pat. 1,472
Patented May 1, 1956

1,472

PEACH TREE

Grant Merrill, Red Bluff, Calif.

Application March 17, 1955, Serial No. 495,078

1 Claim. (Cl. 47—62)

This invention relates to a new and distinct variety of peach tree which bears large, yellow fleshed freestone fruit which is commercially desirable, especially by reason of an extremely late ripening period.

The fruit of the present variety is distinguishable from other late ripening peaches in that the flesh is relatively juicy rather than mealy or dry, and the color thereof is bright yellow in contrast to the greenish cast of many of such other varieties.

Another characteristic of the present variety of peach tree is that the flesh of the fruit does not oxidize and darken upon exposure to air, and the fruit is therefore well adapted for freezing or late canning use.

In comparison to the Merrill Fiesta peach (United States Plant Patent 1,099) the instant variety bears fruit which is nearly as well exteriorly colored and almost as juicy of flesh, but ripens usually about thirty days later.

In comparison to the Elberta peach (unpatented) the instant variety ripens usually about seventy days later.

I originated the present variety of peach tree on my ranch near Red Bluff, Tehama County, California, in the following manner:

The Candoka peach (United States Plant Patent No. 51) was crossed with the Rio Oso Gem peach (United States Plant Patent No. 84), and a number of the seeds of such cross were planted. One of the resulting seedlings appeared promising in its fruit characteristics and was thus selected for possible breeding purposes, but was found to be commercially undesirable because it was self-sterile. Subsequently, a number of seeds from open-pollinated blossoms of such seedlings were planted, and one of the seedlings of this subsequent planting was observed—when it came into bearing—to ripen very late, and yet had good quality for market, shipping, freezing, and canning use.

The last named seedling was therefore selected for reproduction; asexual reproduction having been accomplished by budding onto mature Golden Jubilee (unpatented) peach trees in an orchard on my ranch located as aforesaid.

These asexual reproductions were found to carry forward each and every characteristic of the parent seedling.

Figures 1, 2:
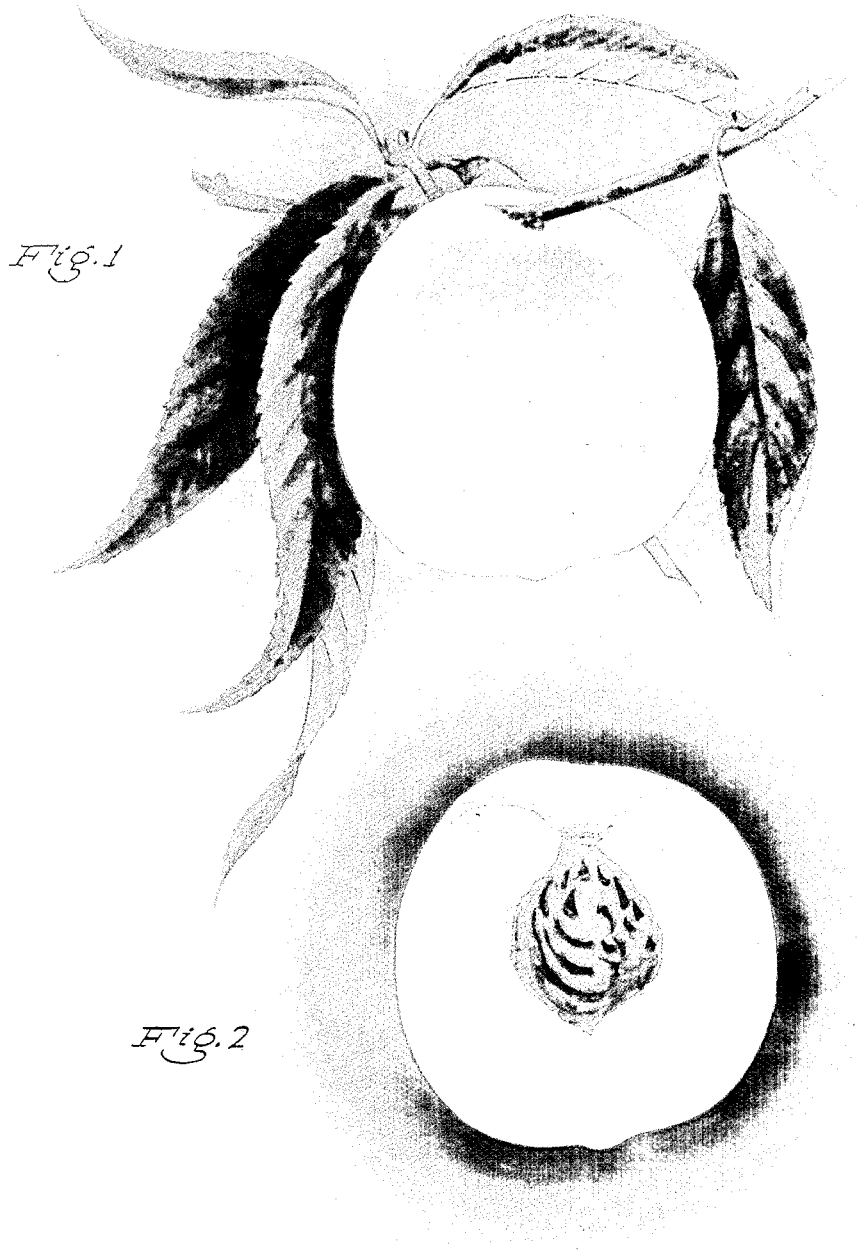
Fig. 1 is an elevation of one of the fruit, together with twigs and leaves.
Fig. 2 is a sectional elevation of one of the fruit, with the stone exposed.

Referring now more specifically to the pomological details of this new and distinct variety of peach tree, the following is an outline description thereof; all major color plate identifications being by reference to Maerz and Paul Dictionary of Color:

Tree:
- *Size.*—Medium.
- *Vigor.*—Medium vigorous.
- *Growth.*—Medium upright.
- *Density.*—Medium dense.

- *Shape.*—Normally pruned to vase form.
- *Production.*—Productive.
- *Bearing.*—Regular bearer.

Trunk:
- *Size.*—Medium stocky.
- *Surface.*—Medium shaggy.

Branches:
- *Size.*—Medium stocky.
- *Surface.*—Medium shaggy.
- *Color.*—Medium brown to reddish brown.
- *Lenticels.*—Medium size.

Leaves:
- *Size.*—Medium. Average length 5″ to 7″. Average width 1″ to 1¾″.
- *Form.*—Lanceolate; tip acuminate; medium thin.
- *Surface.*—Smooth, except along midrib, which is moderately rugose.
- *Margin.*—Crenate.
- *Petiole.*—Medium.
- *Glands.* — None to seven, mostly two to three. Alternate. Medium to small. Reniform. On lower part of leaf and upper part of petiole. Brown to green.
- *Stipules.*—On new growth falling off early.
- *Color.*—Top side—medium green (22–L–9). Under side—lighter green (22–I–6). Midrib on under side yellowish green (18–K–2).

Flower buds:
- *Size.*—Medium.
- *Length.*—Medium.
- *Form*—Plump; free.
- *Pubescence.*—Pubescent.

Flowers:
- *Blooming period.*—Mid season as compared to other varieties.
- *Date of first bloom.*—March 4, 1954.
- *Date of full bloom.*—March 16, 1954.
- *Size.*—Medium.
- *Pollen.*—Present.
- *Color.*—Pink with salmon tinge. Unopened anthers—reddish orange.

Fruit:
- *Maturity when described.*—Firm to eating ripe.
- *Date of first picking.*—October 11, 1954.
- *Date of last picking.*—October 18, 1954.
- *Size.*—Fairly uniform. Large. Average diameter axially—2½″ to 3½″. Average transversely in suture plane—2⅝″ to 3¾″. Average cheek to cheek—2½″ to 4″.
- *Form.*—Globose. Truncate at stem end and slightly cuspidate at apex.
- *Suture.*—Distinct. Extends from base to apex, with slight depression beyond pistil point.
- *Ventral surface.*—Rounded; slightly lipped; lips unequal.
- *Cavity.*—Rounded. Elongated in suture plane with suture showing on both sides. Average depth—⅜″ to ½″. Average breadth—1″. Markings—yellow under-color; some to heavy red blush on most fruit.
- *Base.*—Truncate.
- *Apex.*—Cuspidate.
- *Pistil point.*—Apical.

Skin:
- *Texture.*—Medium thickness; medium tender; sweet. Fairly tenacious to flesh.
- *Tendency to crack.*—None.
- *Down.*—Scant.
- *Color.*—Bright yellow under-color (9–1–4 shading to 9–K–5), with one-fourth to one-half of the peach having a red blush (3–I–11) shading to darker red (6–L–6) adjacent the base end; such blush being mostly mottled but with some striping. A greyish white bloom or sheen overspreads a substantial portion of the yellow under-color.

Flesh:

*Surface of pit cavity.*—Yellow and brown, some pink showing.

*Fibers.*—Pink to brown; abundant.

*Amygdalin.*—Moderate.

*Juice.*—Moderate.

*Texture.*—Firm to meaty; slightly coarse.

*Ripens.*—Evenly.

*Flavor.*—Sub-acid to mild.

*Aroma.*—Distinct.

*Eating quality.*—Good. Not mealy or dry as compared to most late peaches, with considerable juice for a late peach.

*Color.*—Yellow (9–J–2), shading to darker (9–L–6) next to the skin, mottled with red (1–F–10 shading to 1–J–10) next to the stone.

Stone:

*Type.*—Free.

*Adherence to flesh.*—Adheres slightly on ventral edges near base.

*Fibers.*—Short.

*Size.*—Medium. Average length—1½″ to 1¾″. Average breadth—1″ to 1¼″. Average thickness—¾″ to 1″.

*Form.*—Obovate. Tip acuminate.

*Base.*—Oblique.

*Hilum.*—Oval.

*Apex.*—Cuspidate.

*Sides.*—Unequal.

*Surface.*—Irregularly furrowed toward apex. Pitted toward base.

*Ridges.*—Rounded; jagged toward apex; on either side; interrupted.

*Pits.*—Elongated.

*Ventral edge.*—Medium thick.

*Dorsal edge.*—Narrow, with shallow groove toward base.

*Tendency to split.*—Slight in wet weather.

*Color.*—Reddish brown (6–E–12).

Use: Market; local; shipping; canning; freezing.

Keeping quality: Good.

Shipping quality: Good.

The tree and its fruit herein described may vary in slight detail due to climatic and soil conditions under which the variety may be grown, and the method of growing, including pruning and thinning.

The following is claimed:

A new and distinct variety of peach tree, as illustrated and described, which bears large, yellow fleshed, freestone fruit characterized by a late ripening period, a bright yellow exterior color mottled and streaked with red adjacent the base, and relatively juicy flesh which does not darken upon exposure to air; further characterized—in comparison to the Merrill Fiesta peach—by fruit which is nearly as well exteriorly colored and almost as juicy of flesh, but ripens usually about thirty days later; and additionally characterized—in comparison to the Elberta peach—by a ripening period usually about seventy days later.

No references cited.